US005732714A

United States Patent [19]

Morrissey et al.

[11] Patent Number: 5,732,714
[45] Date of Patent: Mar. 31, 1998

[54] ADAPTER FOR USE WITH APPARATUS AND METHOD FOR CONTROLLING HUMAN LACTATION

[76] Inventors: Gerald Morrissey; Suzanne Morrissey, both of 3 Lake View Cir., Skaneateles, N.Y. 13152

[21] Appl. No.: 692,984

[22] Filed: Aug. 7, 1996

Related U.S. Application Data

[63] Continuation of Ser. No. 396,704, Mar. 1, 1995, abandoned, which is a continuation-in-part of Ser. No. 954,012, Sep. 30, 1992, Pat. No. 5,394,889.

[51] Int. Cl.⁶ .................................................. A61G 15/00
[52] U.S. Cl. .................................. 128/846; 128/890
[58] Field of Search .......................... 128/845, 889, 128/890, 846; 604/366, 370, 377, 378, 381, 383; 2/2; 450/36–41, 47, 57, 63, 68, 72, 80, 81, 86–88

[56] References Cited

U.S. PATENT DOCUMENTS

| 65,978 | 6/1867 | Wilder | 128/890 |
|---|---|---|---|
| 077,393 | 4/1868 | McLaughlin | 128/890 |
| 196,594 | 10/1877 | Patch | 128/890 |
| 751,415 | 2/1904 | Prindle | 128/890 |
| 1,165,275 | 12/1915 | Montgomery | 128/890 |
| 1,671,342 | 5/1928 | Cantor . | |
| 2,495,307 | 1/1950 | Abramson | 128/890 |
| 2,834,352 | 5/1958 | Ullian . | |
| 2,891,544 | 6/1959 | London . | |
| 4,164,228 | 8/1979 | Weber-Unger | 128/890 |
| 4,195,639 | 4/1980 | Lee | 128/890 |
| 4,333,471 | 6/1982 | Nakai . | |
| 4,566,458 | 1/1986 | Weinberg . | |
| 4,870,977 | 10/1989 | Imonti . | |
| 4,875,492 | 10/1989 | Mitchell, et al. . | |
| 5,032,103 | 7/1991 | Larsson . | |
| 5,171,321 | 12/1992 | Davis | 128/890 |

FOREIGN PATENT DOCUMENTS

| 1133702 | 4/1957 | France . |
|---|---|---|
| 377643 | 6/1921 | Germany . |
| 177295 | 3/1922 | United Kingdom . |

OTHER PUBLICATIONS

Pg. 78 in *The Womanly Art of Breast Feeding*, J. Torgas, ed., La Leche League International, New York, N.Y. (1987).

Primary Examiner—Michael A. Brown
Attorney, Agent, or Firm—Nixon, Hargrave, Devans & Doyle

[57] ABSTRACT

An adapter for use with an apparatus for the control of human lactation. The apparatus comprising a support having an outer surface and an inner surface that is shaped to conform substantially to a human female breast and having a protrusion which extends away from the support and is positioned to align substantially with a nipple of a human female. The adapter comprises an attachment having a second outer surface and a second inner surface. The second outer surface has a second protrusion extending away from the second outer surface and is shaped to fit over the first protrusion. The second inner surface is positioned to align substantially with and contact a nipple of the human female breast to prevent the human female breast from lactating when the apparatus with the adapter is placed over the human female breast.

18 Claims, 6 Drawing Sheets

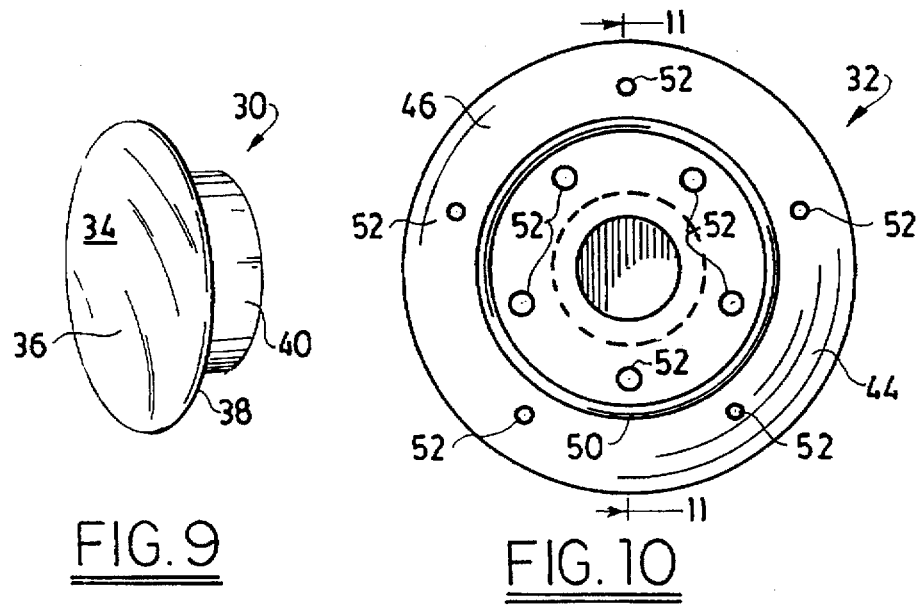
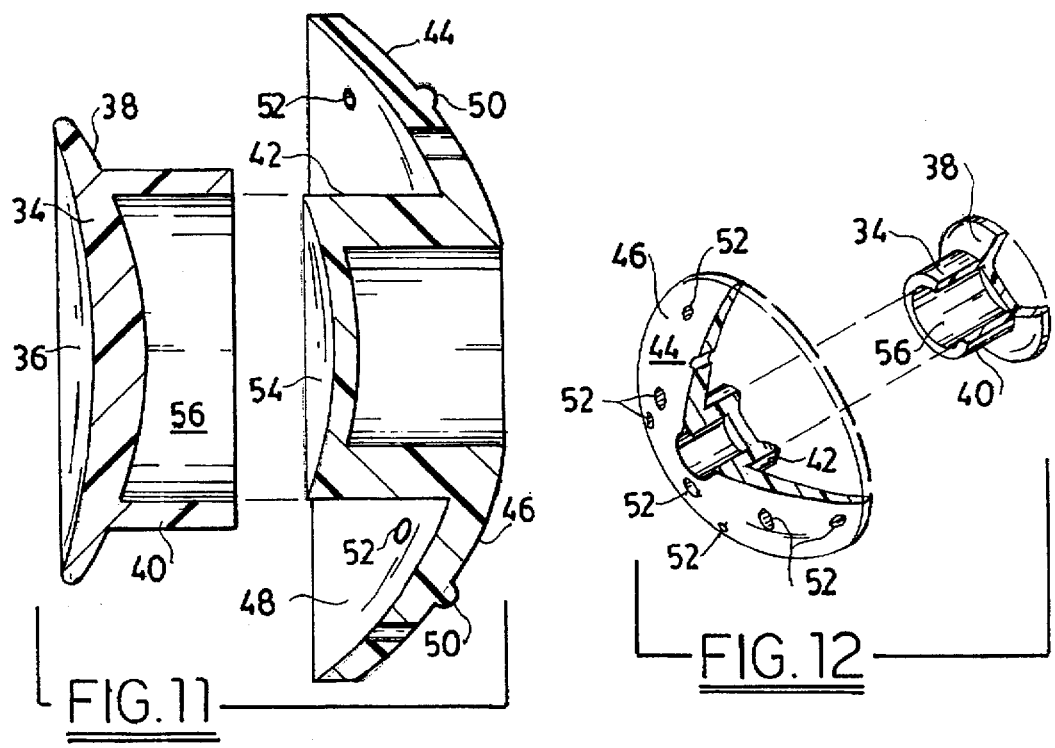

5,732,714

ADAPTER FOR USE WITH APPARATUS AND METHOD FOR CONTROLLING HUMAN LACTATION

FIELD OF INVENTION

This application is a continuation of 08/396,704 filed Mar. 1, 1995, now abandoned, which is a continuation-in-part of application Ser. No. 07/954,012, filed on Sep. 30, 1992, now U.S. Pat. No. 5,394,889. The present invention relates to an adapter for use with an apparatus and method for controlling and/or stopping lactation in human females.

BACKGROUND OF THE INVENTION

In recent years, breastfeeding of newborn babies has seen a resurgence in popularity. Breastfeeding is becoming more popular for a variety of reasons relative to both baby and mother. These advantages include increased protection of the infant from illness through the development of protective antibodies, decreased risk of developing childhood cancers, avoiding potential allergies to commercial infant formulas, and enhanced jaw, teeth, and speech development, among others. Furthermore, it has been suggested that nursing mothers have a lower risk of developing breast cancer. Breast feeding has also been suggested to improve the emotional bond between mother and child.

Although breast feeding is enjoying renewed use, it is not without disadvantages. The outpouring of milk is known as the "let-down" or "milk-ejection" reflex. A let-down can occur several times during a feeding. It is well known that the milk-ejection reflex can be triggered at inappropriate times by various stimuli. A baby's crying, for example, may cause let-down in a nursing mother. This can result in let-down at very inopportune times.

This inappropriate let-down can be particularly problematic for working mothers who are nursing. Solutions designed to alleviate problems associated with inappropriate let-down include absorbent breast pads or breast shields that operate, essentially, as a well or reservoir to collect leaking milk. These solutions are disadvantageous because of the limited capacity of both types of devices as well as the likelihood that milk will leak into clothing despite their use.

It is also known that nursing mothers can apply direct pressure to the nipples with the heels of their hands or forearms to temporarily halt leakage. However, this type of solution likewise presents obvious disadvantages for the nursing mother who is working or otherwise in public.

An additional problem in controlling lactation is that the size of women's nipples vary. The size variations are due to genetics and also due to changes during and after pregnancy at which time the size of nipples for mothers swell. To ensure that milk ejection will be suppressed substantially all of the exposed nipple must be compressed.

In addition to controlling lactation, stopping lactation in women, who for personal or medical reasons have decided not to breastfeed and want to dry up has also been difficult. One option for stopping lactation has been the use of drug therapy, however the use of drug therapy has come under intense scrutiny because of the serious side effects these drugs have produced. The other existing option to stop lactation has been a binding process. Elastic bandages are tightly wrapped around a woman's body covering her breasts and nipples. The bandages can potentially stop lactation, but put severe pressure on the woman's back and mammary glands which is very uncomfortable and can have negative side effects (i.e., mastitis, plugged ducts).

Therefore, there continues to be a need for an apparatus and/or an apparatus with an adapter that can effectively control and/or stop lactation in nursing mothers by a safe and effective method.

SUMMARY OF THE INVENTION

An apparatus for controlling or stopping human lactation includes a support having an outer surface and an inner surface that is shaped to conform substantially to a human female breast and having a first protrusion which extends away from the support and is positioned to align substantially with a nipple of a human female. An adapter for use with the apparatus includes an attachment having a second outer surface and a second inner surface. The second outer surface of the adapter has a second protrusion which extends away from, the second outer surface and is shaped to fit over the first protrusion for the apparatus. The second inner surface is positioned to align substantially with and contact a nipple of the human female breast to prevent the human female breast from lactating when the apparatus with the adapter is placed over the human female breast.

The apparatus and method of the present invention, with and without the adapter, provide a convenient and effective way to prevent inopportune milk leakage in the nursing mother. The adapter enables nursing mothers to adjust the size of the nipple contact surface to their particular nipple size so that the nipple is covered and leakage is controlled. The apparatus and method, with or without the adapter, are also effective to stop a woman from lactating by applying constant pressure to the nipple until the woman dries up naturally. The apparatus and the adapter can be inexpensively constructed in a variety of shapes from a variety of materials.

BRIEF DESCRIPTION OF THE DRAWINGS

FIG. 9 is a perspective view of an adapter in accordance with the present invention;

FIG. 10 is a perspective view of an outer surface of another embodiment of the apparatus with the adapter;

FIG. 11 is an exploded, cross-sectional view of the apparatus and adapter taken along line 11—11 in FIG. 10;

FIG. 12 is a cut-away, exploded, perspective view of the apparatus and adapter shown in FIG. 11;

DETAILED DESCRIPTION OF THE INVENTION

Figure 1:
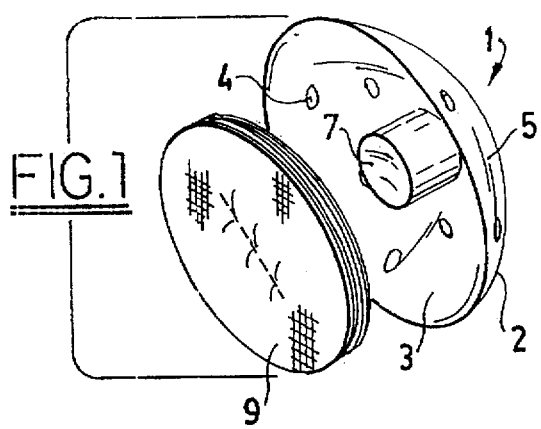
FIG. 1 is an exploded, perspective view of one embodiment of the apparatus of the present invention and an absorbent breast pad.
Figure 3:
FIG. 3 is a side view of an absorbent breast pad.
Figure 2:
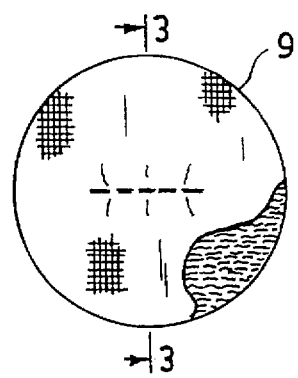
FIG. 2 is a front view of an absorbent breast pad.
Figure 7:
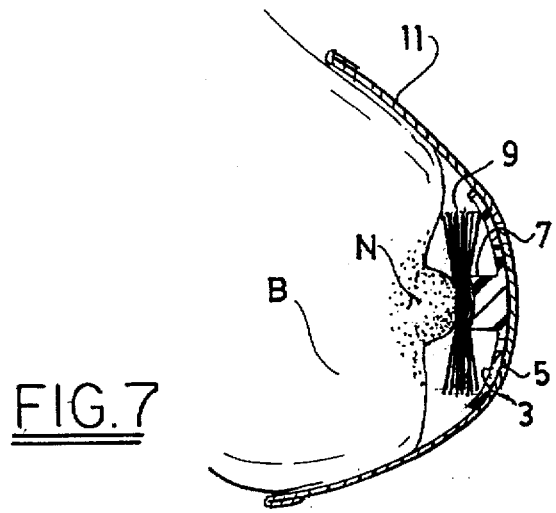
FIG. 7 is a cross-sectional side view of the apparatus, including a brassiere, placed over a human female breast.

FIG. 1 is an exploded, perspective view of one embodiment of the apparatus of the present invention and an absorbent breast pad. Apparatus 1 includes support 2 having an inner surface 3 and an outer surface 5. Inner surface 3 has a protrusion 7 which extends away from support 2. Referring to FIG. 7, which is a cross-sectional side view of one embodiment of the present apparatus, including a brassiere, placed over a human breast, protrusion 7 is positioned to align substantially with and contact nipple N of human female breast B. Protrusion 7 operates to depress nipple N, whereby breast B is prevented from lactating.

Support 2 is shaped to conform substantially to a human female breast. Support 2 can, for example, be substantially circular with a concave/convex shape covering a relatively small area of breast B as shown in FIG. 7. Support 2 can also take a variety of other forms, substantially conforming to larger or smaller areas of breast B. Preferably, support 2 is constructed in a substantially circular, concave/convex form and having a radius from about 3 to 5 inches for maximum comfort and to allow use of the apparatus on breasts of various sizes. Most preferably, support 2 is shaped such that suction is created between breast B and apparatus 1 after apparatus 1 is placed over breast B. The suction helps to maintain the alignment of apparatus 1 with nipple N.

Figure 4:
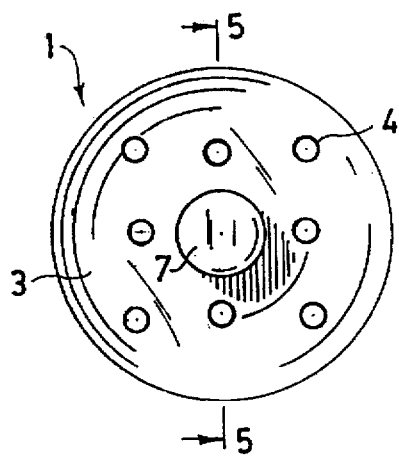
FIG. 4 is a perspective view of the inner surface and protrusion of the apparatus.
Figure 6:
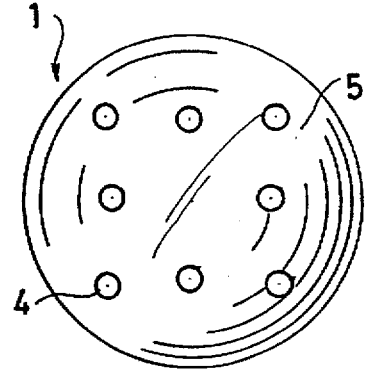
FIG. 6 is a perspective view of the outer surface of the support of the apparatus.

Support 2 can be made from a variety of flexible materials including moldable plastic or rubber. Preferably, the support is made from a moldable, flexible plastic material to allow maximum comfort and ease of manufacture. With reference to FIGS. 4 and 6, perspective views of the inner and outer surfaces, respectively, of support 2, support 2 can be provided with holes 4 to allow air circulation around the nipple and areolar region of breast B to help prevent local irritation which commonly occurs in nursing mothers.

Figure 5:
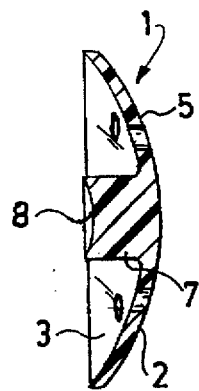
FIG. 5 is a cross-sectional side view of FIG. 4 taken along line 5—5.

Protrusion 7 can be produced separately and then attached to inner surface 3 or, preferably, integrated with inner surface 3. This preferred embodiment is shown by FIG. 5, a cross-sectional side view of FIG. 4 taken along line 5—5. Protrusion 7 can be integrated with inner surface 3 by molding protrusion 7 and support 2 together from the same material. Protrusion 7 can be made from a variety of materials, as long as the material is sufficiently rigid to depress nipple N when nipple N is contacted by protrusion 7. Exemplary materials for forming protrusion 7 include any of the rigid plastics known in the art or sufficiently rigidized rubber.

Figure 8:
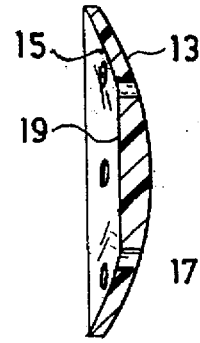
FIG. 8 is a cross-sectional side view of an alternative embodiment of the inner surface of the support and protrusion of the present invention.

Protrusion 7 can be any shape, so long as it is capable of depressing nipple N when apparatus 1 is brought into contact with breast B and, in turn, preventing lactation. For example, protrusion 7, can be a flattened, planar surface formed in the center of the inner surface 3 of support 2, as shown by FIG. 8, a cross-sectional side view of an alternative embodiment of the inner surface of the support and protrusion of the present invention. Protrusion 7 is preferably cylindrical, having a size approximating a human female nipple, as shown in FIG. 7. Most preferably, as illustrated by FIGS. 7 and 9, nipple-contacting surface 8 of protrusion 7 is concave to make the apparatus more comfortable for the wearer and aid in keeping apparatus 1 in place.

Preferably, absorbent pad 9 is placed over inner surface 3 to absorb any small amount of leakage resulting, for example, from misalignment of protrusion 7 and nipple N as well as any other moisture surrounding the nipple and areolar region. This embodiment is illustrated by FIGS. 1 and 7.

As shown by FIG. 7, the above-described apparatus can be used by placing it over breast B and applying pressure to the apparatus sufficient to depress and, in turn, prevent milk release by nipple N of breast B. The amount of pressure need not be great and can normally be produced by the force provided when apparatus 1 further comprises brassiere 11. Support 2 can be placed inside the cup of brassiere 11 which is then put on by the lactating woman, as illustrated by FIG. 7. Support 2 can either be manually placed into or actually integrated with (e.g., sewn into) the cup of the brassiere. Brassiere 11 can be a conventional or nursing brassiere commonly worn by nursing mothers.

Referring to FIG. 9, a perspective view of an adapter 30 which can be used in conjunction with apparatus 32 (shown in FIGS. 10 and 11) is illustrated. Adapter 30 includes an attachment 34 with inner and outer surfaces 36 and 38. In this particular embodiment, inner surface 36 has a substantially concave shape and outer surface 38 has a substantially convex shape (shown more clearly in FIG. 11), although inner and outer surfaces 36 and 38 can have other shapes, as described later with respect to FIGS. 18 and 21. Inner surface 36 is used to contact with the nipple N of the lactating woman. Adapter 30 expands the surface area which engages with the nipple N. The larger adapters 30 cover women who have larger nipples due to genetics or due to swelling before or after pregnancy. Lactation is only prevented if the nipple is substantially covered and depressed. By way of example only, nipple contacting surface 8 on protrusion 7 in FIG. 5 has a diameter of about ¾", but when adapter 30 is added to apparatus 1 or 32 the diameter of inner surface 36 of adapter 32 is increased to about 1¾". The particular size of adapter 30 can vary as desired.

Outer surface 38 of adapter 32 also includes a protrusion 40 which extends away from outer surface 38 and is shaped to fit over protrusion 42 of support 44. Protrusions 40 and 42 are described in greater detail below with respect to FIGS. 11 and 12.

Referring to FIG. 10, a perspective view of an outer surface 46 of apparatus 32 with adapter 30 attached to apparatus 32 is illustrated (Adapter 30 is not visible from this view). Apparatus 32 includes support 44 with an inner surface 48 (shown in FIG. 11), outer surface 46, a raised ring 50, and a plurality of air holes 52. In this particular embodiment, support 44 has a substantially circular shape, although support 44 could have other shapes, such as oval. Support 44 can be made from a variety of materials, including plastic and rubber.

Figure 16:
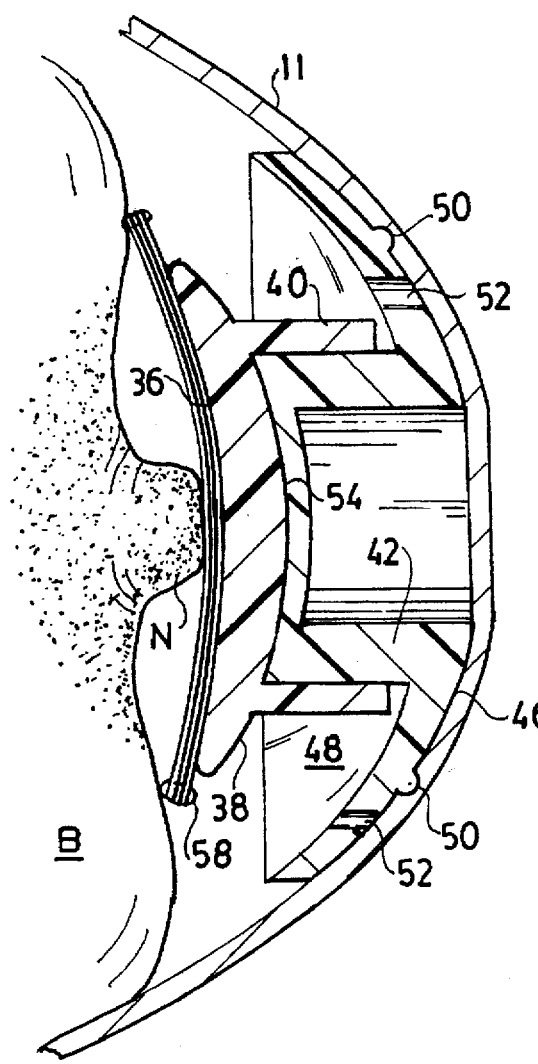
FIG. 16 is a cross-sectional, side view of the apparatus and adapter, including a brassiere and the absorbent breast pad, placed over a human female breast.

Raised ring 50 extends out and away from outer surface 46 of support 44. When apparatus 32 is disposed in the cup of brassiere 11, as shown in FIG. 16, raised ring 50 catches against the inside of the cup to help keep support 44 and adapter 30 in place against the woman's breast B. Although only one raised ring 50 is shown, support 44 can have as may raised rings 50 on outer surface 38 as desired.

Referring to FIGS. 10 and 16, air holes 52 extend through support 44 between outer and inner surfaces 46 and 48 to allow air to circulate to the woman's breast B to prevent local irritation. The number of air holes 52 is increased from that shown for support 2 in FIGS. 4 and 6 so that even more air can circulate through to the breast B. Apparatus 32 and adapter 30 can be used not only to control lactation, but also to stop lactation. To stop lactation, apparatus 32 and adapter 30 must be worn by the lactating woman for extended periods of time until the woman dries up naturally. To make the use of apparatus 32 and adapter 30 more comfortable, particularly for women using apparatus 32 and adapter 30 to stop lactating, the additional air holes 52 were added. Although ten air holes 52 are shown, the number of air holes can vary as desired.

Referring to FIG. 11, an exploded, cross-sectional view of apparatus 32 and adapter 30 taken along line 11—11 in FIG. 10 is illustrated. Corresponding elements in FIG. 11 have numeral designations which correspond to those designations used in FIG. 7 and will not be described again here. Protrusion 42 has a substantially cylindrical shape which extends out and away from inner surface 48 of apparatus 32 to an end 54 which is substantially concave, although the shape of protrusion 42 and end 54 can vary as desired. In this particular embodiment, protrusion 42 has a diameter of about ¾".

Another protrusion 40 which has a substantially cylindrical shape extends out and away from outer surface 38 of adapter 30. Preferably, protrusion 40 is integrated with support 34, although protrusion 40 could be produced separately and then attached to outer surface 38 of support 34. Protrusion 40 also has a substantially cylindrical opening 56 shaped to fit snugly over protrusion 42 of support 34. The diameter of opening 56 is slightly larger than the diameter of protrusion 42. As shown in the exploded, cut-away view in FIG. 12, the opening in protrusion 56 fits over and against the outside of protrusion 42. The friction between the opening 56 in protrusion 40 and the outside of protrusion 42 holds adapter 30 in place. Although protrusion 40 and opening 56 both have a cylindrical shape, protrusion 40 and opening 56 could have other shapes, such as square or triangular. Protrusion 40 is designed to fit far enough over protrusion 42 so that even when adapter 30 is attached to apparatus 32, adapter 30 does not add significantly to the overall width of apparatus 32 and adapter 30.

Figure 13:
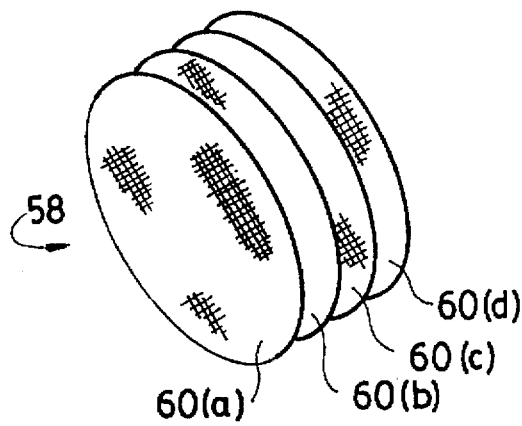
FIG. 13 is an exploded, perspective view of another embodiment for the absorbent breast pad.
Figure 14:
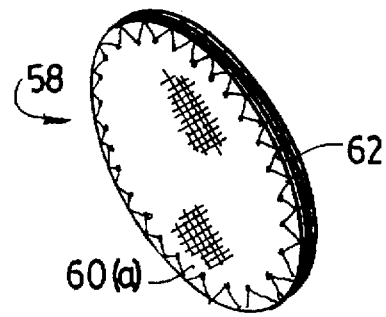
FIG. 14 is a perspective view of the absorbent breast pad shown in FIG. 13.

Referring to FIGS. 13 and 14, optional absorbent breast pad 58 includes four layers 60 (a–d) of absorbent material which are joined together by stitching 62 along an outside edge of layers 60 (a–d). In this particular embodiment, each layer 60 (a–d) has a substantially circular shape and is made from cotton, although other shapes and materials could be used. If additional layers were added, then the thickness of pad 58 would cause adapter 30 and apparatus 32 to slip out of place, if fewer layers were used, then pad 58 would provide less comfort to the user.

Figure 15:
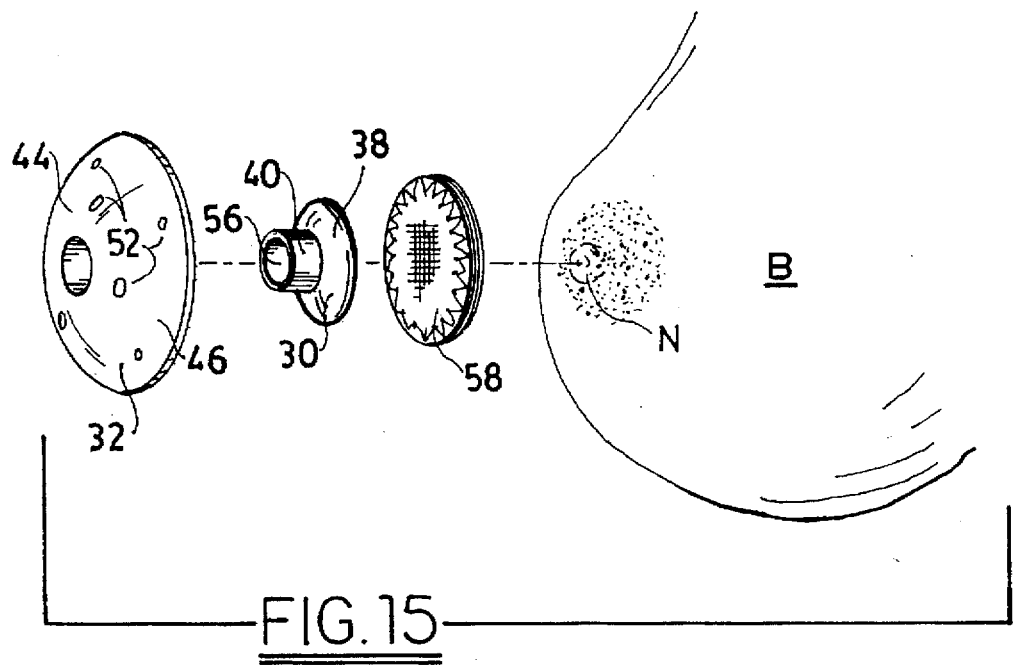
FIG. 15 is an exploded, perspective view of the apparatus, adapter, absorbent breast pad being positioned to be placed over a human female breast.
Figure 19:
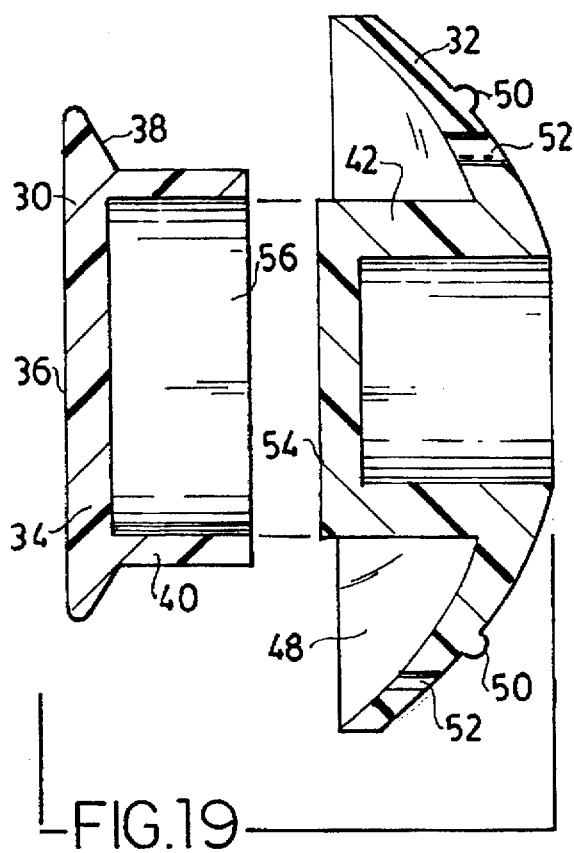
FIG. 19 is an exploded, cross-sectional, side view of the apparatus with the adapter shown in FIG. 18.
Figure 20:
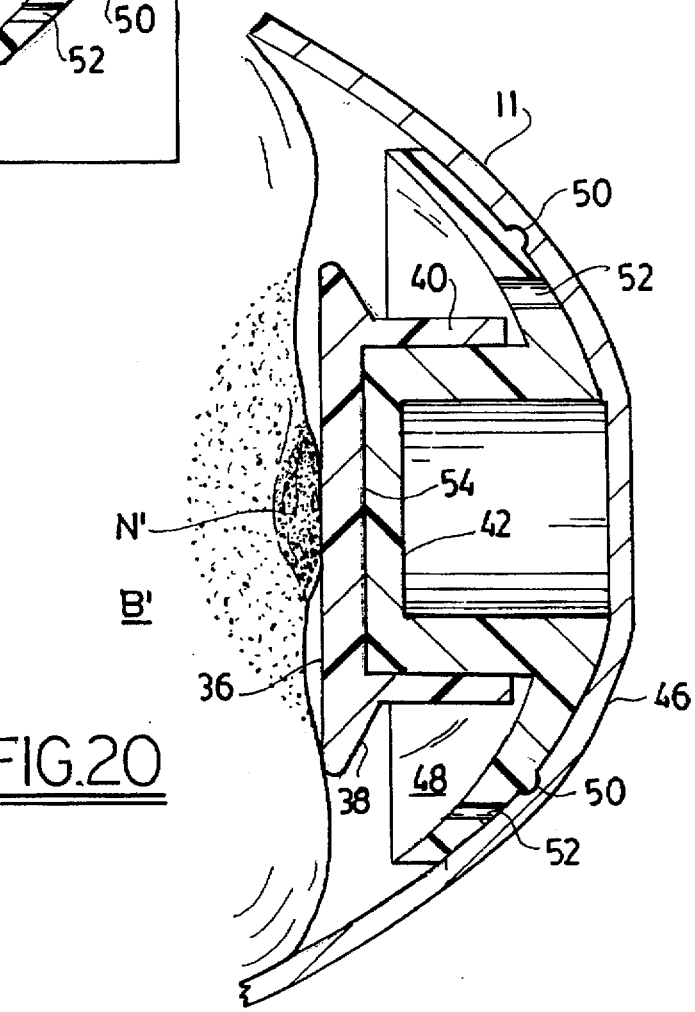
FIG. 20 a cross-sectional, side view of the apparatus with the adapter shown in FIG. 18.

Referring to FIGS. 15 and 16, the use of apparatus 32 with adapter 30 and absorbent breast pad 58 is illustrated. First, if the woman's nipple N is larger then end 54 of protrusion 42 of support 44, then adapter 30 is selected and protrusion 40 of adaptor 30 is placed over protrusion 42 of apparatus 32 to attach adapter 30 to apparatus 32. If the woman's nipple N is not inverted (as shown in FIG. 16), then an adapter 30 with a substantially concave, inner surface 36 is selected. The substantially concave, inner surface 36 surrounds the nipple N and areolar region and helps to keep adapter 30 in place. If the woman's nipple is inverted N', as shown in FIG. 20, or flat (not shown), then an adapter 30 with a substantially flat or convex, inner surface 36 (shown and described later with respect to FIGS. 18–22) is selected.

Next, outer surface 46 of support 44 with adapter 30 in place is placed inside and against the cup of brassiere 11. Raised ring 50 holds support 44 and adapter 30 in place against brassiere 11 due to friction. Although not shown, support 44 with adapter 30 may be integrated with (e.g., sewn into) the cup of brassiere 11. Once apparatus 32 with adapter 30 is in place, then brassiere 11 is put on by the woman locating apparatus 32 and adapter 30 over breast B and, in particular, locating substantially concave, inner surface 36 of adapter 30 against nipple N. Optional absorbent breast pad 58 may be placed between breast B and substantially concave, inner surface 36 of adapter 30 before or after brassiere 11 is in place. Absorbent breast pad 58 absorbs any small leakage or excess moisture and makes adapter 30 and apparatus 32 more comfortable against breast B. Once apparatus 32 and adapter 30 are in place against breast B, brassiere 11 applies sufficient pressure on substantially concave, inner surface 36 of adapter 30 to depress nipple N preventing the release of milk.

Figure 17:
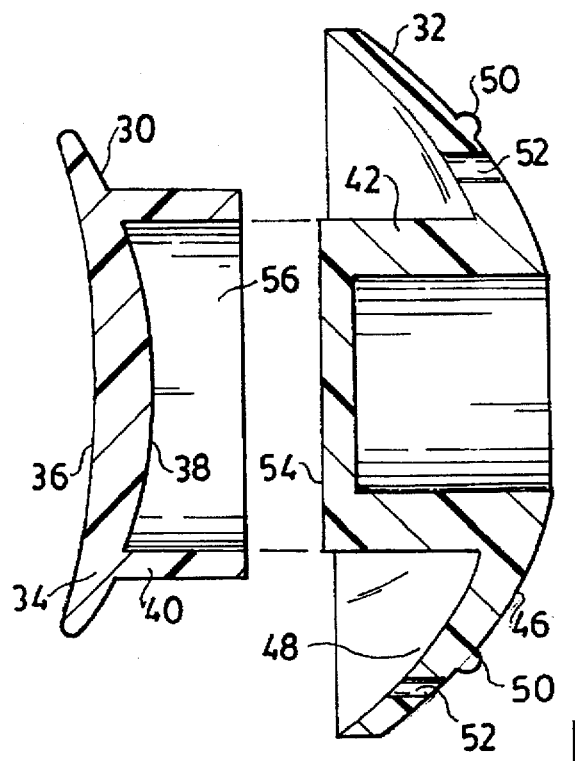
FIG. 17 is an exploded, cross-sectional view of the apparatus with the adapter.

Preferably, outer surface 38 of adapter 30 in opening 56 in protrusion 40 is shaped to substantially conform to the shape of end 54 of protrusion 42 of support 44, as shown in FIGS. 11, 16, 19, and 21. However, the shape of outer surface 38 does not have to conform to end 54 of protrusion 42. Referring to FIG. 17, the shape of outer surface 38 is convex and does not substantially conform to the substantially flat, shape of end 54 of protrusion 42 of support 44. Nevertheless, the frictional engagement of the inside of opening 56 of protrusion 40 with the outside of protrusion 42 holds adapter 30 in place.

Figure 18:
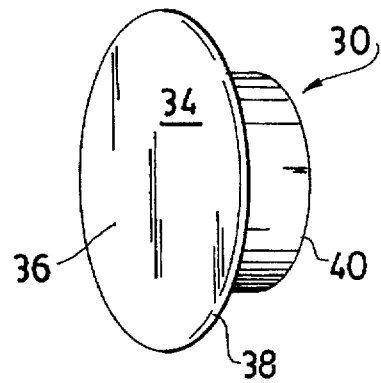
FIG. 18 is a perspective view of another embodiment for the adapter.

Referring to FIG. 18, a perspective view of another embodiment for adapter 30 is illustrated. Corresponding elements in FIG. 18 have numeral designations which correspond to those designations used in FIG. 9 and will not be described again here. In this particular embodiment, inner surface 36 of adapter 30 is substantially flat. The substantially flat shape for inner surface 36 is desirable for preventing lactation from woman with at least one inverted nipple N', as shown in FIG. 20 or flat nipple. With an inverted nipple or flat nipple, apparatus 32 with adapter 30 having a substantially flat, inner surface 36 is preferable over apparatus 32 with adapter 30 having a concave, inner surface 36. If the latter apparatus 32 and adapter 30 were used, the outer edges of concave, inner surface 36 would dig into the areolar region of the breast. With substantially flat, inner surface 36, the inverted nipple N', as shown in FIG. 20, or flat nipple (not shown) is compressed without undue pressure from the edge of inner surface 36 cutting into the areolar region. As shown in FIG. 19, outer surface 38 of adapter 30 in opening 56 of protrusion 40 is substantially flat to conform to substantially flat, end 54 of protrusion 52.

Referring to FIG. 20, the use of apparatus 32 with another embodiment for adapter 30 is illustrated. Corresponding elements in FIG. 20 have numeral designations which correspond to those used in FIG. 16 and will not be described here again. In this particular embodiment, the woman's breast B' has an inverted nipple N'. Accordingly, an adapter 30 with a substantially flat, inner surface 36 is used to comfortably compress inverted nipple N' to prevent lactation, without applying undue pressure on the areolar region. In this particular embodiment, optional absorbent breast pad 58 is not used. Although adapter 30 with a substantially flat, inner surface 36 is shown, adapter 30 with a substantially convex inner surface 36, as shown in FIGS. 21 and 22, could have been used.

Figure 21:
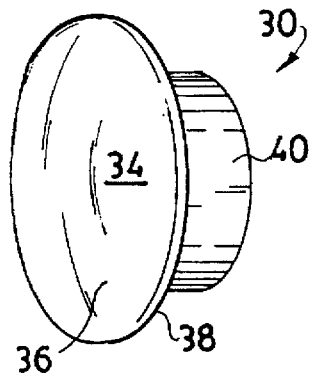
FIG. 21 is a perspective view of yet another embodiment for the adapter.
Figure 22:
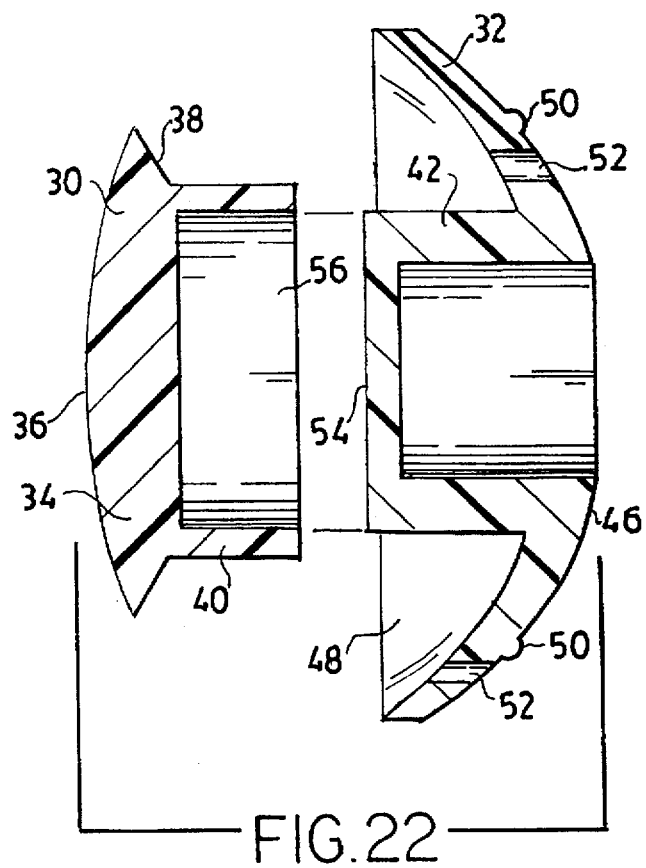
FIG. 22 is an exploded, cross-sectional view of the apparatus with the adapter shown in FIG. 21.

Referring to FIG. 21, a perspective view of yet another embodiment for adapter 30 is illustrated. Corresponding elements in FIG. 21 have numeral designations which correspond to those designations used in FIG. 9 and will not be described again here. Although the preferred shape for inner surface 36 of adapter 30 for non-inverted nipples is substantially concave and for inverted nipples is substantially flat, in this particular embodiment, inner surface 36 has a substantially convex shape. The convex shape of inner surface 36 may also be used on an inverted nipple to apply pressure to prevent lactation, however the substantially convex shape will not stay in place against the inverted nipple as well as the substantially flat shape. As shown in FIG. 22, outer surface of adapter 30 in opening of protrusion 40 is substantially flat to conform to the substantially flat, end of protrusion 42.

Although the invention has been described in detail, for the purpose of illustration, it is understood that such detail is for that purpose and variations can be made therein by those skilled in the art without departing from the spirit and scope of the invention which is defined by the following claims.

What is claimed is:

1. An adapter for use with an apparatus for the control of human lactation, said adapter comprising an attachment having an outer surface and an inner surface, said inner surface being substantially smooth over substantially all of said inner surface, said outer surface having a protrusion extending away from said outer surface to an end, said protrusion having an opening which extends in from said end towards said outer surface.

2. The adapter according to claim 1, wherein said nipple-contacting inner surface has a substantially concave shape.

3. The adapter as set forth in claim 1 wherein said opening in said second protrusion extends substantially down to said outer surface.

4. The adapter as set forth in claim 1 wherein said second protrusion and said opening each have a substantially cylindrical shape.

5. An adapter for use with an apparatus for the control of human lactation, said adapter comprising an attachment having an outer surface and a nipple-contacting inner surface, said outer surface having a protrusion extending away from said outer surface to an end, said protrusion having an opening which extends in from said end towards said outer surface, wherein said inner surface has a substantially convex shape.

6. An adapter for use with an apparatus for the control of human lactation, said adapter comprising an attachment having an outer surface and a nipple-contacting inner surface, said outer surface having a protrusion extending away from said outer surface to an end, said protrusion having an opening which extends in from said end towards said outer surface, wherein said inner surface has a substantially flat shape.

7. A method for controlling human lactation comprising the steps of:
providing an apparatus comprising a support having a first outer surface and a first inner surface that is shaped to conform substantially to a human female breast, said first inner surface having a first protrusion extending away from said support;
providing an adapter comprising an attachment having a second outer surface and a second inner surface, said second outer surface having a second protrusion extending away from said second outer surface and shaped to fit over said first protrusion;
placing said second protrusion over said first protrusion;
placing said apparatus over said breast;
positioning said apparatus to align said second inner surface substantially with and contact said nipple of said breast; and
applying pressure to said apparatus sufficient to prevent said breast from lactating.

8. The method according to claim 7, wherein said second inner surface has a substantially convex shape.

9. The method according to claim 7, wherein said second inner surface has a substantially concave shape.

10. The method according to claim 7, wherein said second inner surface has a substantially flat shape.

11. The method according to claim 7, wherein said second inner surface is substantially the same size as said nipple.

12. The method according to claim 7, wherein said second inner surface is substantially larger than said nipple.

13. An apparatus for the control of human lactation comprising a support having a first outer surface and a first inner surface having a substantially concave shape, said first inner surface having a first protrusion extending away from said support and positioned to align substantially with a nipple of said human female breast when said apparatus is placed over said human female breast, and an adapter having a second outer surface and a second inner surface, said second outer surface having a second protrusion extending away from said second outer surface and shaped to fit over said first protrusion and said second inner surface positioned to align substantially with and contact a nipple of said human female breast to prevent said human female breast from lactating when said apparatus is placed over said human female breast.

14. The apparatus according to claim 13, wherein said second inner surface has a substantially convex shape.

15. The apparatus according to claim 13, wherein said second inner surface has a substantially concave shape.

16. The apparatus according to claim 13, wherein said second inner surface has a substantially flat shape.

17. The apparatus according to claim 13, further comprising an absorbent breast pad placed on said inner surface of said support.

18. The apparatus according to claim 17, wherein said absorbent breast pad comprises four layers.

* * * * *